(12) United States Patent
Moon et al.

(10) Patent No.: US 9,757,410 B2
(45) Date of Patent: *Sep. 12, 2017

(54) FLEXIBLE POLY-P-(PHENYLENEETHYNYLENE)S WITH CONTROLLED CONJUGATION LENGTH AND BIODEGRADABLE CONJUGATED POLYMERS FOR TARGET ORGANELLE SPECIFIC LABELING AND DRUG DELIVERY

(71) Applicants: Joong Ho Moon, Weston, FL (US); Rajeshkumar Manian, Miami, FL (US); Eladio Mendez, Miami, FL (US)

(72) Inventors: Joong Ho Moon, Weston, FL (US); Rajeshkumar Manian, Miami, FL (US); Eladio Mendez, Miami, FL (US)

(73) Assignee: THE FLORIDA INTERNATIONAL UNIVERSITY BOARD OF TRUSTEES, Miami, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 15/000,232

(22) Filed: Jan. 19, 2016

(65) Prior Publication Data

US 2016/0206751 A1 Jul. 21, 2016

Related U.S. Application Data

(60) Provisional application No. 62/104,992, filed on Jan. 19, 2015.

(51) Int. Cl.

| A61K 47/48 | (2006.01) |
| A61K 31/728 | (2006.01) |
| C08G 61/12 | (2006.01) |
| C08B 37/08 | (2006.01) |
| C08L 5/08 | (2006.01) |
| C08G 69/42 | (2006.01) |
| B82Y 30/00 | (2011.01) |

(52) U.S. Cl.
CPC ........ *A61K 31/728* (2013.01); *C08B 37/0072* (2013.01); *C08G 61/12* (2013.01); *C08G 61/121* (2013.01); *C08L 5/08* (2013.01); *B82Y 30/00* (2013.01); *C08G 69/42* (2013.01); *C08G 2261/12* (2013.01); *C08G 2261/126* (2013.01); *C08G 2261/143* (2013.01); *C08G 2261/1424* (2013.01); *C08G 2261/18* (2013.01); *C08G 2261/19* (2013.01); *C08G 2261/312* (2013.01); *C08G 2261/3328* (2013.01); *C08G 2261/415* (2013.01); *C08G 2261/5222* (2013.01); *C08G 2261/74* (2013.01); *C08G 2261/94* (2013.01)

(58) Field of Classification Search
CPC .............................. C08F 238/02; A61K 47/48
USPC ......................... 528/396; 526/285; 525/54.2
See application file for complete search history.

(56) References Cited

PUBLICATIONS

U.S. Appl. No. 14/821,890 Claims, Aug. 2015.*
Hay, M. et al., "Aliphatic Phenylene Vinylene Copolymers: Tuning the Color of Luminescence through Co-monomer Feed Ratios," *J. Am. Chem. Soc.*, 1995, p. 7112-7118, vol. 117.
Huang, S. et al., "Rapid Bi-directional Synthesis of Oligo(1,4-phenylene ethynylene)s," *Tetrahedron Letters*, 1999, pp. 3347-3350, vol. 40.
Kang, S. et al., "Controlled Catalyst Transfer Polycondensation and Surface-Initiated Polymerization of a p-Phenyleneethynylene-Based Monomer," *J. Am. Chem. Soc.*, 2013, pp. 4984-4987, vol. 135.
Kovalev, A.I. et al., "Chain Growth Polycondensation as a Polymer Generating Reaction in the Synthesis of Oligo(p-phenyleneethynylene)s with Low Polydispersity," *Macromol. Chem. Phys.*, 2005, pp. 2112-2121, vol. 206.
Li, N. et al., "Theoretical Study of Spectroscopic Properties of Dimethoxy-p-Phenylene-Ethynylene Oligomers: Planarization of the Conjugated Backbone," *J. Phys. Chem. A*, 2007, pp. 9393-9398, vol. 111.
Vanveller, B. et al., "Poly(aryleneethynylene)s", *Design and Synthesis of Conjugated Polymers*, 2010, pp. 175-200.

* cited by examiner

*Primary Examiner* — Duc Truong
(74) *Attorney, Agent, or Firm* — Saliwanchik, Lloyd & Eisenschenk

(57) ABSTRACT

A novel monomer design for the synthesis of PPE-type polymers containing conjugated segments of well-defined length connected by flexible linkers under Sonogashira reaction conditions is presented. The resulting polymers retain the photophysical properties of a fully conjugated PPE. The extent of incorporation of the flexible units along the backbone is governed by the comonomer feed ratio and can be varied in a statistically predictable fashion.

12 Claims, 16 Drawing Sheets

Before and after HA complexation

Absorbance (arb)

FLEXIBLE POLY-P-(PHENYLENEETHYNYLENE)S WITH CONTROLLED CONJUGATION LENGTH AND BIODEGRADABLE CONJUGATED POLYMERS FOR TARGET ORGANELLE SPECIFIC LABELING AND DRUG DELIVERY

CROSS-REFERENCE TO A RELATED APPLICATION

This application claims the benefit of U.S. Provisional Application Ser. No. 62/104,992, filed Jan. 19, 2015, the disclosure of which is hereby incorporated by reference in its entirety, including all figures, tables and drawings.

This invention was made with government support under GM092778 and DMR1352317 awarded by the National Institute of Health and the National Science Foundation, respectively. The government has certain rights in the invention.

BACKGROUND OF INVENTION

The synthesis of conjugated oligomers with precisely controlled, well-defined conjugation length is valuable for fine tuning of the physical and photo-physical properties of conjugated polymers. A series of oligomers of precisely controlled structure can be used as a model for the investigation of processes governing the physical and photophysical properties of the corresponding larger, polydisperse polymeric materials. Monodisperse conjugated oligomers contain minimal structural defects compared to the polymers, and allow greater control of the material's electronic properties. The synthesis of well-defined oligomers typically requires multi-step approaches utilizing multiple iterations of protection/deprotection chemistry and purification at each step, making such synthesis very low yielding. The development of one-pot synthetic methods towards oligomers with well-defined conjugation length is highly desirable.

Among conjugated polymers (CPs), poly(p-phenyleneethynylene)s (PPEs) are a class of bright, fluorescent materials with excellent physical and photophysical properties and emerging applications in solar cell electronics, fluorescence analyte sensing, imaging, and targeted cellular delivery of therapeutics.

The synthesis of conventional PPEs utilizes the palladium-mediated Sonogashira coupling reaction between aryl halides and terminal alkynes (AABB-type polymerization). The polymerization under these conditions proceeds in a stepwise manner, requires a high degree of stoichiometric balance, and results in an alternating A-B-type polymer, as indicated in Scheme 1, below, typically with a relatively large polydispersity index.

Scheme 1. A general scheme for the formation of PPEs via Sonogashira coupling

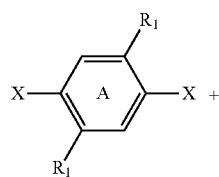
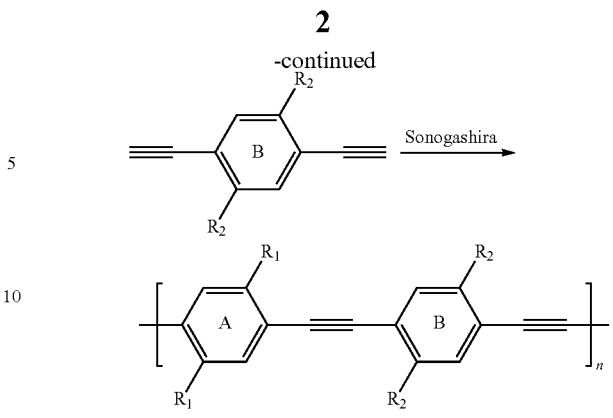

Several approaches to the synthesis of oligo-PPEs have explored different features of the Sonogashira reaction. These include the intentional breaking of stoichiometric balance, differences in reactivity between different aryl halides, Huang et al., *Tetrahedron Lett.* 1999, 40, 3447-3450, polymer end-group activation, Kovalev et al., *Macromol. Chem. Phys.* 2005, 206, 2112-2121, and catalyst transfer polycondensation, Kang, et al., *J. Am. Chem. Soc.* 2013, 135, 4984-4987. More precise control can be achieved by step-by-step or convergent synthesis utilizing a series of protection, coupling and deprotection steps, VanVeller et al., "Poly(aryleneethynylene)s" pages 175-200 in Design and Synthesis of Conjugated Polymers, M. Leclerc, J. Morin (Eds.) Wiley-VCH: Weinheim, 2010. All of the above approaches require multiple purification steps, and are thus time-consuming, low-yielding and costly.

Labeling and monitoring of biological substances and activities in live cells are crucial for understanding complex biological systems, and can permit development of biological/biomedical sensors or therapeutic means for various diseases. Small fluorescent molecules have been used for labeling and sensing of various cellular substances including nucleic acids, proteins, intracellular organelles, whole cells, and tissues. Small molecular weight compounds often use passive diffusion mechanism to enter cells. There are several issues resulting from the high concentrations required to create a concentration gradient between cellular membranes. High concentration can cause non-specific labeling, thus increasing background signals. High concentrations can increase cellular toxicity. Small compounds for in vivo delivery and labeling display extremely poor efficiency due to poor pharmacokinetic properties.

Semiconducting conjugated polymer nanoparticles (CPNs) are emerging fluorescent biomaterials that have been employed for labelling, sensing, and delivery of biological substances. Owing to their fluorescent and lipophilic nature, CPNs are a unique mitochondrial delivery platform that can facilitate understanding of how chemical structures affect the uptake behavior of these polymeric vehicles. CPNs as mitochondrial delivery vehicles are presently limited to formulations with liposomal vehicles.

Polymeric nanoparticles (NPs) can overcome many limitations of concentration and in vivo properties of small molecules. NPs permit various endocytosis pathways to enter cells, and relatively small quantity can be used for labeling of target cells with no need for a concentration gradient. Since NPs are brighter than a typical single fluorescent molecule, high local fluorescent intensities are possible from NPs. However, NPs are very inefficient for labeling of intracellular molecules and organelles because of their high molecular weight.

Hence it is desirable to combine small molecule and NP intracellular targeting advantages. Hence it is desirable to synthesize biodegradable conjugated polymer nanoparticles (CPNs) that can be taken up by cells as NPs and degraded into small fluorescent molecules that label target intracellular organelles.

PPE polymers can be tailored to a specific application through the modulation of their physical, biological and optical properties by structural modifications of the rigid conjugated backbone and the pendant side-chains. More specifically, it would be advantageous if controlled introduction of flexibility into the CP backbone could be carried out with the retention of the optical properties of the fully conjugated PPE polymer while improving the material's solubility, modulating its aggregation properties, or including a biodegradable component for intercellular applications. A flexible content could translate to the formation of segments of shorter conjugation length, and the precise control of the amount of flexibility provides a means to control the length of conjugated segments within a polymer chain. Such a backbone structure could modify complexation with polyanions, and dramatically impact cellular uptake and subcellular localization of conjugated polymer nanoparticles (CPNs). It has not been possible to control the amount of flexible component in PPEs due to the nature of the catalytic system (Glaser coupling).

BRIEF SUMMARY

Embodiments of the invention are directed to monomers and their polymerization to PPEs such that conjugated segments of well-defined length are connected by flexible linkers under Sonogashira reaction conditions. In embodiments of the invention, the flexible linkers can be sites for biodegradability of the PPEs into relatively small oligomers. Advantageously, the resulting polymers retain the photophysical properties of a fully conjugated PPE. The extent of incorporation of the flexible units along the backbone is governed by the comonomer feed ratio and can be varied in a statistically predictable fashion.

The synthetic method involves few synthetic steps and permits easy purification. These defect free conjugated materials perform better than equivalent CPs with defects. The resulting CPs allow precise color tuning. The one-pot synthetic method is beneficial for material fabrication for diverse applications. In an embodiment of the invention, biodegradable CPs for gene/drug delivery with controlled release at targeting can be prepared.

Biological imaging and delivery applications can be addressed with the CPs. Drugs, genes, and/or labeling molecules can be delivered using CPNs that release their payloads to a targeted site. By controlled degradation, CPNs permit controlled release and specific labeling of cells and organelle while fluorescent monitoring the cell treatment.

BRIEF DESCRIPTION OF THE FIGURES

FIG. 3B is a composite of normalized emission spectra of polymers P1, P2, P4 and P6 in DMF for various co- and terpolymer PPEs according to an embodiment of the invention.

FIG. 10C and FIG. 10D show composite absorption and emission spectra, respectively, of uncomplexed and hyaluronic acid complexed PPE, according to an embodiment of the invention.

FIG. 19A shows subcellular co-localization changes as a function of time from endosome to mitochondria, while FIG. 19B shows that co-localization remains constant regardless of incubation time.

DETAILED DISCLOSURE

Figure 1:
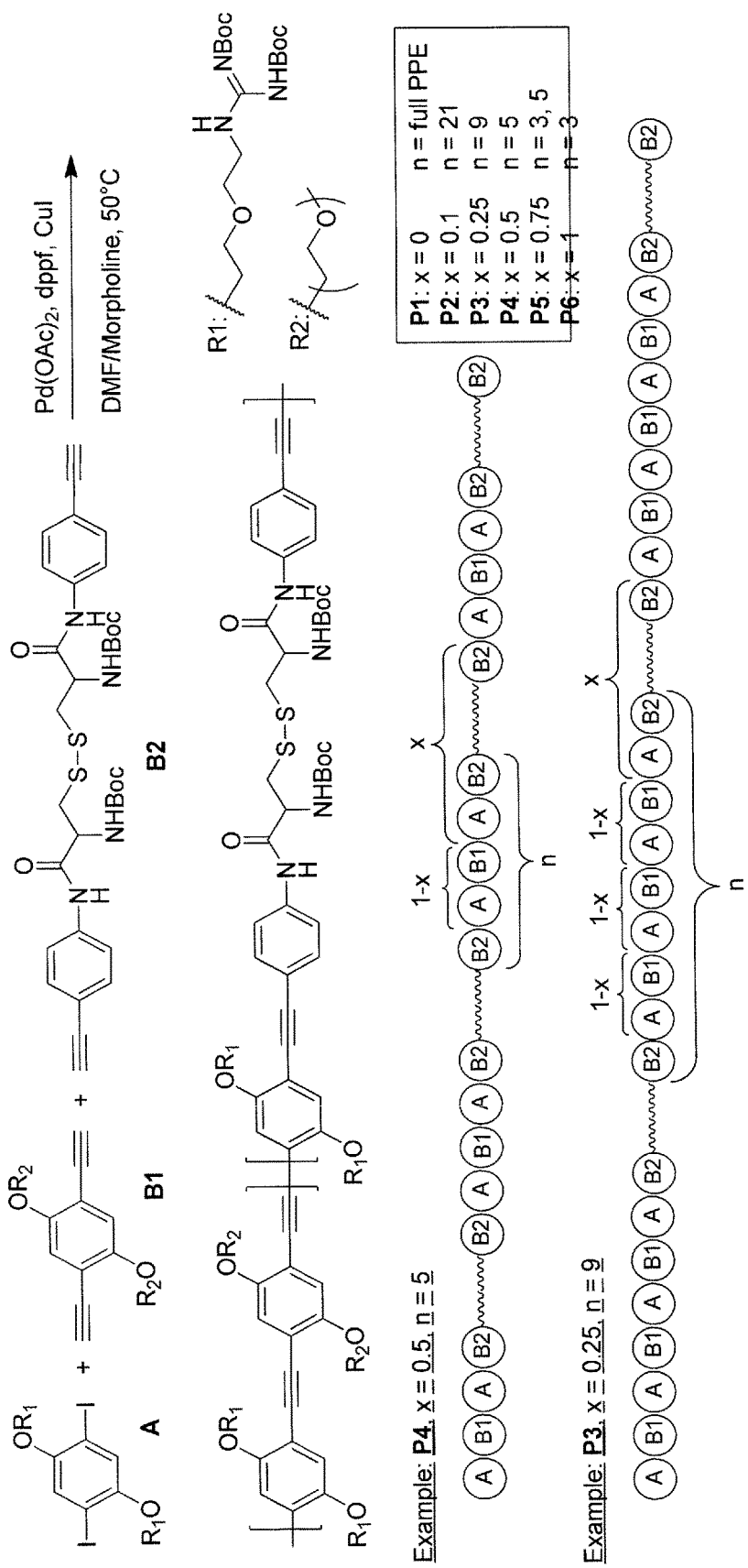
FIG. 1 is a reaction scheme for the preparation of terpolymer PPEs having a flexible linker according to an embodiment of the invention.

Embodiments of the invention are directed to monomers and their polymerization to PPEs such that conjugated segments of well-defined length are connected by flexible linkers under Sonogashira reaction conditions. In embodiments of the invention, the flexible linkers can be sites for biodegradability of the PPEs into relatively small oligomers. Advantageously, the resulting polymers retain the photophysical properties of a fully conjugated PPE. The extent of incorporation of the flexible units along the backbone is governed by the comonomer feed ratio and can be varied in a statistically predictable fashion. Increased flexible content translates to the formation of segments of shorter conjugation length, and the precise control of the amount of flexibility therefore provides a means to control the length of conjugated segments within a polymer chain. In an embodiment of the invention, the flexible spacer provides biodegradability to the PPE. By increasing the proportion of flexible units at the expense of the conjugated ones leads to the formation of shorter conjugated segments, and the conjugated length can thus be shortened in a statistically predictable fashion. Optical properties of the fully conjugated backbone are preserved in polymers with flexible content less than 25%. The incorporation of a variable proportion of a flexible monomer into a polymer formed under Sonogashira conditions requires the use of three monomers with one A-type monomer and a desired ratio of two different B-type monomers.

Stoichiometric incorporation of the flexible unit into the CP backbone under Sonogashira conditions requires minimal if any Glaser-type homocoupling, which is controlled by the monomer structure and by optimizing reaction conditions. Since the monomer reactivity towards the Sonogashira reaction is heavily governed by the choice of aryl halide and the electronic substitution of its aromatic ring, the proportion of the aryl iodide monomer A was kept constant to the B-type monomer throughout an exemplary polymer series. The ratio of acetylene comonomers B1 (conjugated) and B2 (flexible) was varied to achieve the controlled conjugation length modulation, as indicated in the reaction scheme shown in FIG. 1.

The reactivity of the acetylene monomer towards Sonogashira coupling is enhanced by the inclusion of electron-donating groups to promote nucleophilicity toward copper acetylide, which increases the rate of the transmetalation step. The p$K_a$s for the B1 and B2 acetylene protons are, however, very similar, 23.4 and 23.7 respectively; hence, electronic effects would not be expected to be a contributing factor towards reactivity differences.

In an embodiment of the invention, monomer A has ethylene oxide side-chains containing pendant guanidinium groups. The guanidinium group is an amine-rich functionality naturally occurring in the amino acid guanidine, consisting of two delocalized primary amines and one secondary amine with a high p$K_a$ of around 13. This functional group improves solubility and cellular uptake.

The flexible diacetylene monomer B2, according to an embodiment of the invention, is based on modified cystine, a naturally occurring biomolecule. In addition to its non-conjugated, flexible nature, it provides a biodegradable moiety useful for intracellular gene delivery. The fully conjugated complementary diacetylene monomer B1 has long ethylene oxide chains to promote polymer solubility.

Optimization of the polymerization conditions was carried out in order to find a suitable system for the incorporation of the biodegradable, flexible, disulfide-containing monomer B2. The initial polymerization of B2 with aryl iodide A to yield P6, as shown in FIG. 1, which is a polymer with the highest possible flexible content under typical Sonogashira conditions using Pd[Cl$_2$(PPh$_3$)$_2$], CuI, DMF/morpholine, did not yield polymers with considerable molecular weight. It appears that B2 inhibits the Sonogashira coupling reaction through complexation with the palladium species, where the monomer acts as a bidentate ligand coordinating through the sulfur and nitrogen atoms. Sonogashira reactions often use ligands to accompany the palladium source for improved catalytic cycle efficiency. To counteract this effect, according to an embodiment of the invention, ligand with stronger affinity than B2 towards palladium is introduced to overcome the effect of the disulfide-containing monomer.

A screening of polymerizations using monomers A and B2 under systematically varied combinations of Pd[Cl$_2$(PPh$_3$)$_2$], Pd[(PPh$_3$)$_4$] and Pd(OAc)$_2$ with bidentate ligands 1,4-bis(diphenylphosphino)-butane (dppb), 1,1'-bis(diphenylphosphino) ferrocene (dppf), and 2,2'-bipyridyl (bpy) reveled that the presence of dppf in the coupling reaction greatly improves the resulting polymer molecular weights. Polymerization is effectively carried out using Pd(OAc)$_2$, dppf, CuI, DMF/THF/DIPA in the presence of the disulfide monomer B2.

A series of polymers, as illustrated in FIG. 1, with variable proportion of flexible, non-conjugated biodegradable linker B2 was prepared by varying the relative stoichiometric ratio of monomers B1 and B2 from 1:0 to 0:1. The physical and photophysical properties are summarized in Table 1, below. The flexible content is denoted as "x" and represents the percentage of B2 out of total amount of diacetylene monomer used. The conjugation length is represented by "n" which denotes the number of arylene units within the conjugated segment. For example, P6 is synthesized exclusively from the reaction between monomers A and B2, resulting in a polymer with three consecutive arylene conjugated units connected via the cystine linker. For P6 "x" is therefore 1, and "n" is equal to 3. The total flexible content in P3 would be 50%—a half of the amount of the B2 proportion "x", owing to the fact that the iodo monomer A and the combined acetylenes are always reacted at a 1:1 ratio.

TABLE 1

Comparison of the Physical and Photophysical Properties of polymers P1-P6 with varying conjugation length.

| Polymer | A equiv. | B1 equiv. | B2 (=x) | $n^a$ | $M_n$ (g/mol)[b] | PDI[c] | $\lambda_{max,\ abs}$ (nm)[d] | $\lambda_{max,\ em}$ (nm)[d,e] | QY (%)[f] |
|---|---|---|---|---|---|---|---|---|---|
| P1 | 1 | 1 | 0 | n/a | 18,800 | 1.28 | 441 | 476 | 25 |
| P2 | 1 | 0.90 | 0.10 | 21 | 10,700 | 1.50 | 425 | 473 | 17 |
| P3 | 1 | 0.75 | 0.25 | 9 | 11,800 | 1.47 | 417 | 472 | 20 |
| P4 | 1 | 0.50 | 0.50 | 5 | 12,200 | 1.50 | 399 | 469 | 13 |
| P5 | 1 | 0.75 | 0.25 | 3 + 5 | 5,300 | 1.54 | 361 | 453 | 6 |
| P6 | 1 | 0 | 1 | 3 | 13,400 | 1.70 | 358 | 406 | 5 |

[a] Statistically predominant number of phenylene rings within a conjugated segment.
[b] Determined by gel permeation chromatography in THF.
[c] PDI (polydispersity index) = $M_w/M_n$.
[d] Measured in DMF.
[e] Excitation wavelength 440, 420, 415, 395, 360 and 355 nm in DMF.
[f] Quantum yield in DMF measured relative to diphenylanthracene standard.

Figure 2:
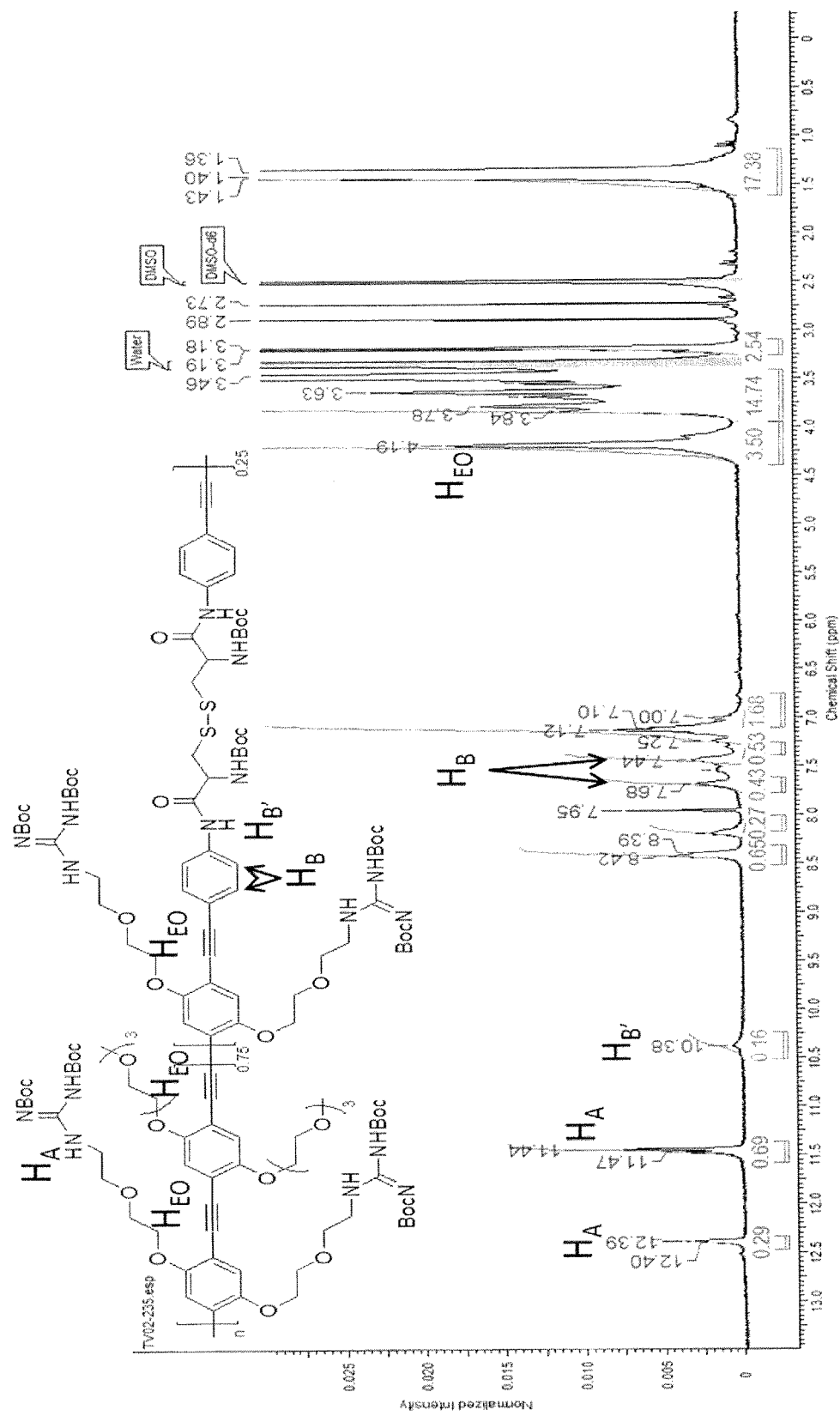
FIG. 2 is a $^1$HNMR spectrum of a terpolymer PPE having a flexible linker according to an embodiment of the invention.

Incorporation of the flexible unit into the exemplary PPEs was evaluated by $^1$H NMR spectroscopy, as shown in FIG. 2. The analysis of predicted copolymer structures examined the alkoxy protons on the side-chain of monomers A and B1 ($H_{EO}$, ~4.2 ppm), the guanidinium NH protons characteristic to monomer A ($H_A$, combination of ~11.4 and ~12.4 ppm), the methoxy protons characteristic to monomer B1 (~3.2 ppm), and the aromatic protons ($H_B$, ~7.45 and ~7.65 ppm) and amine NH ($H_{B'}$, ~40.4 ppm) characteristic to monomer B2. All proton peaks were integrated relative to the ethylene oxide proton peak $H_{EO}$, and were in good agreement with the integration values predicted by theoretical copolymer analysis. An example spectrum of polymer P3 is presented in FIG. 2. Based on the B1:B2 feeding ratio (0.75:0.25), the predicted polymer structure calls for $H_{EO}$ proton integration of 3.5 (0.75*4H+0.25*2H). The observed integrations of the remaining peaks correspond well to the predicted values: for $H_A$, predicted 1H (0.75*1H+0.25*1H), observed 0.98 (0.29+0.69), for $H_B$ predicted 0.5H (0.25*2H), observed 0.48 (average of 0.43 and 0.53), and for $H_{B'}$ predicted 0.25, observed 0.16, presumably due to deuterium exchange with solvent. While $^1$H NMR data point towards stoichiometrically controlled B2 incorporation, the technique only provides information about the average sample, and it is therefore not a reliable tool for the prediction of the length of the individual conjugated segments.

Figure 3A:
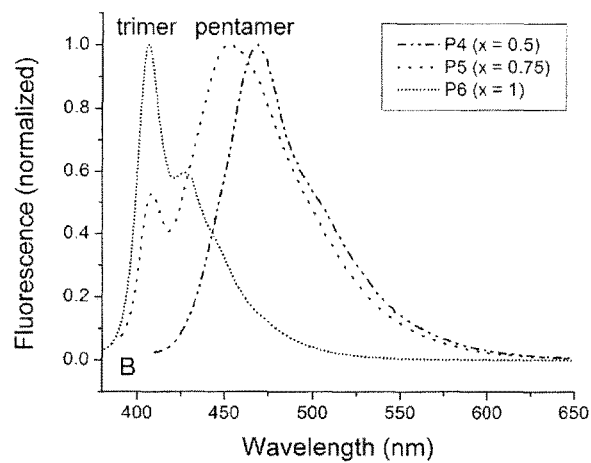
FIGS. 3A-3B show a composite of normalized absorption (FIG. 3A)
Figure 3B:
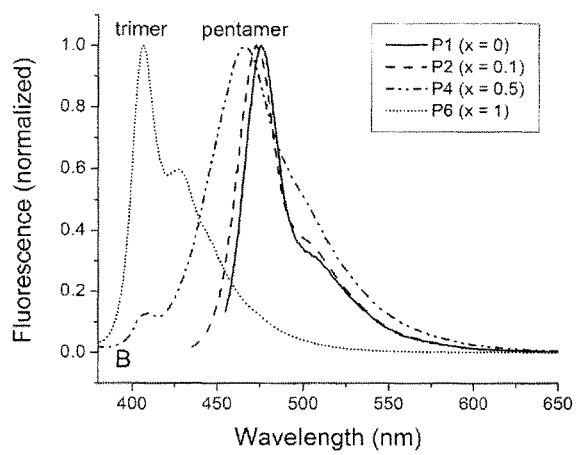

Direct evidence of conjugation length modulation is demonstrated by absorption and emission spectra of the polymers P1-P6, which clearly show a blue shift in absorbance maxima with increasing flexible, non-conjugated linker content (i.e. higher "x", lower "n"), as shown in FIG. 3A. This shift indicates that the predominant conjugated units within the polymers indeed structurally correspond to the average units characterized by NMR. A similar trend is not observed for the fluorescence maxima of the six polymers, as shown in FIG. 3B.

Figure 4:
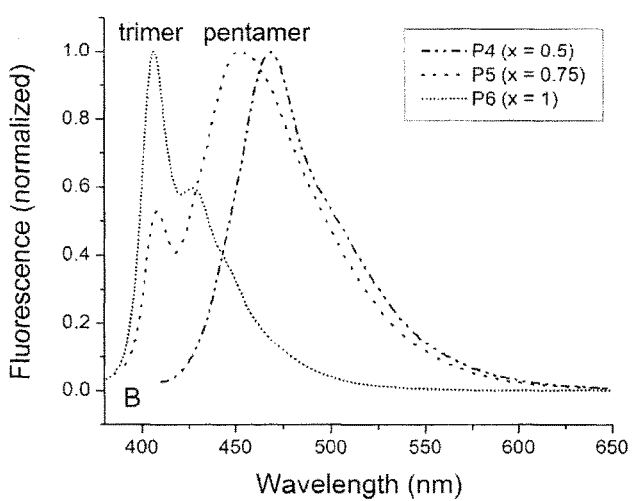
FIG. 4 is a composite of normalized emission spectra of polymers P4, P5, and P6 in DMF according to an embodiment of the invention.

The experimental observations, however, only show this trend with the last three polymers in the series, P4-P6, as shown in FIG. 4. The polymer P6 with the shortest conjugated segments (x=1, n=3) exhibits blue fluorescence at 406 nm as expected, while in polymer P4, in which the B1/B2 feed ratio statistically favors the predominant formation of pentamers (n=5), the emission maximum is significantly red-shifted at 469 nm (>60 nm Stokes shift). Polymer P5, which contains both trimers and pentamers based on the monomer feed ratio (B1:B2 0.25:0.75), shows two emission maxima, one at the wavelength of the trimer (n=3, 408 nm) and one significantly red shifted (453 nm) corresponding to pentamer (n=5). The overlap between the trimer emission and the pentamer absorption maxima (408 nm and 399 nm respectively) leads to resonance energy transfer (RET) from the shorter, higher-energy trimer units to the longer, lower energy pentamers, resulting in the pentamer units being the major emitting species. This explanation is consistent with the observed P5 emission spectrum which features the predominant red-shifted emission at 453 nm. Studies of a structurally related conjugated poly-p-(phenylynevinylene)s (PPVs) display similar effects, Hay et al., *J Am. Chem. Soc.* 1995, 117, 7112-7118. Furthermore, the emission peaks of the shorter polymers undergoing RET are very broad, while polymers with increased conjugation length and consequent decrease of the amount of RET (P1 and P2), vibrational structure can be observed. No further significant red-shifting of emission maxima occurs with additional increase in conjugation length past pentamer (P4→P1), suggesting that the effective conjugation length for this series of PPEs is reached with approximately five aromatic segments. Theoretical calculations on a series of oligo p-phenylene-ethynylenes, Li et al., *The Journal of Physical Chemistry A* 2007, 111, 9393-9398, indicate that the effective conjugation length is saturated at around ten aromatic units, this number decreases to around five when the planarity of the conjugated segment can be disturbed. Thus by keeping the amount of the flexible linker below 25% of the total polymer content, as in P4, one can fabricate flexible polymers with good solubility and the photophysical properties exhibited by fully-conjugated PPE polymer backbones.

Advantageously, this step-growth polymerization, which is expected to be completely random, leads to a series of polymers with a relatively well-defined, predictable pattern of monomer incorporation as evidenced by the UV absorbance trend. One explanation is that a preferential formation of the PPE-conjugated oligomeric segments happens between monomers A and B1, which are subsequently linked up into a polymer in a reaction with B2. The synthesis of polymer P3 was carried out with the sequential addition of monomers. A (1 eq) and B1 (0.75 eq) were allowed to react in the absence of linker B2. The resulting oligomers P3a exhibited photophysical properties similar to the one-pot polymer P3. When we added the remaining monomer B2 (0.25 eq) and additional polymerization proceeded, polymer P3b exhibited an increase in polymer molecular weight relative to oligomers P3a and conserved photophysical properties analogous to those of P3. The number average molecular weight of the polymer P3b more than doubled compared to oligomers P3a, and $^1$H NMR clearly demonstrates the incorporation of linker B2 into the polymer.

TABLE 2

Sequential addition experiment.

| Polymer | A | B1 | B2 | $M_n$ (g/mol) | PDI | $\lambda_{max, abs}$ (nm) | $\lambda_{max, em}$ (nm) | QY (%) |
|---|---|---|---|---|---|---|---|---|
| P1 | 1 | 1 | 0 | 18,800 | 1.28 | 441 | 476 | 25 |
| P3 | 1 | 0.75 | 0.25 | 11,800 | 1.47 | 417 | 472 | 20 |
| P3a | 1 | 0.75 | — | 2,000 | 2.15 | 425 | 476 | 12 |
| P3b | 1 | 0.75 | 0.25 | 5,100 | 1.90 | 420 | 472 | 10 |

Figure 5:
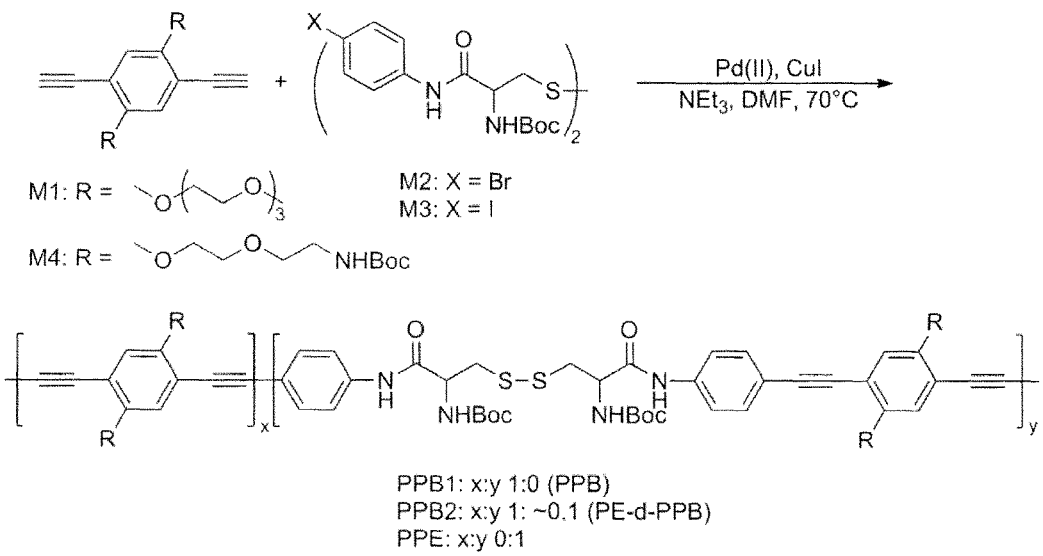
FIG. 5 shows a reaction scheme for an alternate preparation of co- or terpolymer PPEs according to an embodiment of the invention.
Figure 6:
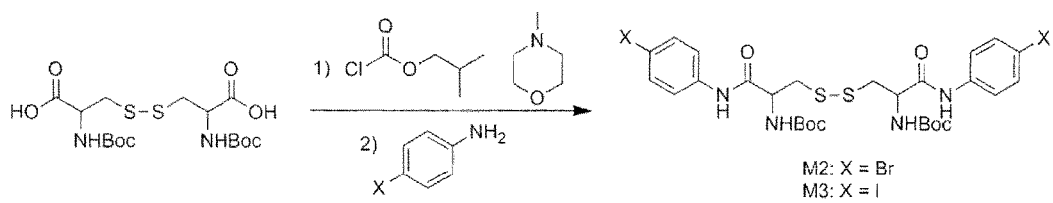
FIG. 6 shows a reaction scheme for the synthesis of a di(haloaryl) flexible spacer according to an embodiment of the invention.
Figure 7:
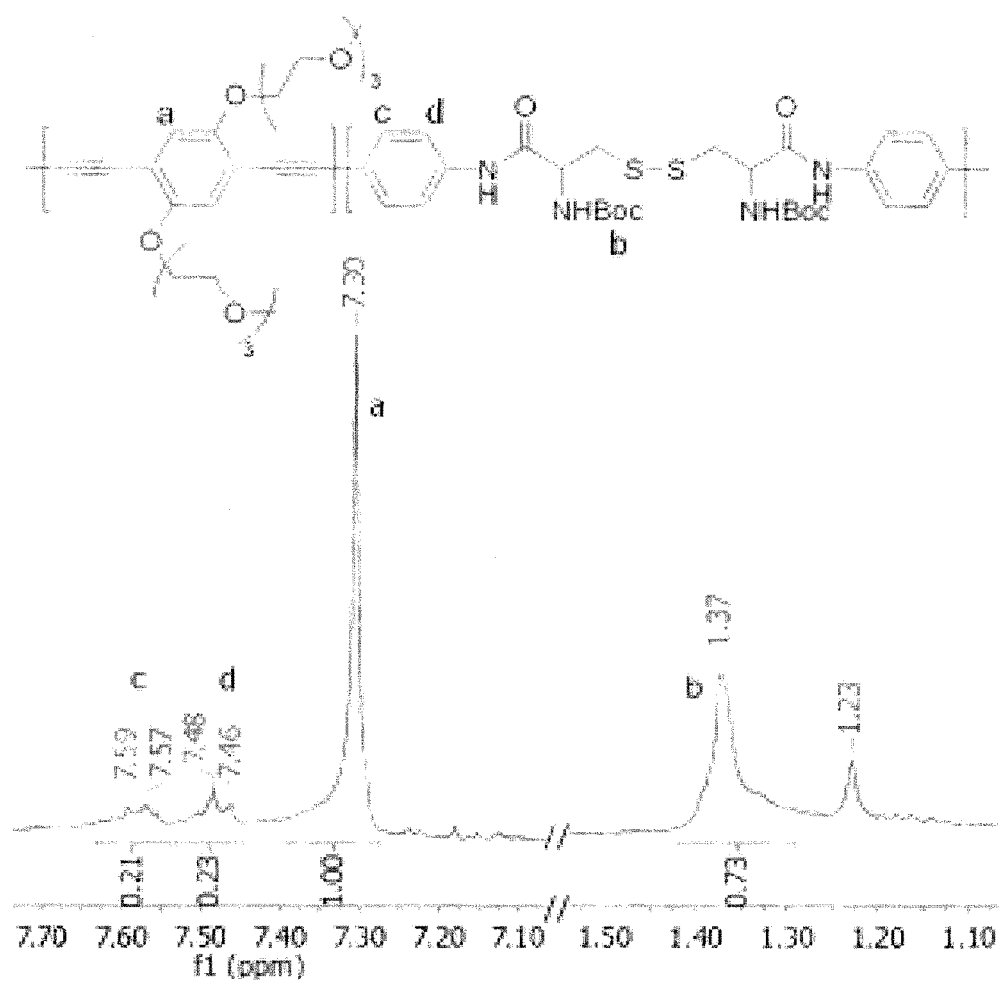
FIG. 7 is a $^1$HNMR spectrum of a terpolymer PPE having a flexible linker according to an embodiment of the invention.
Figure 8A:
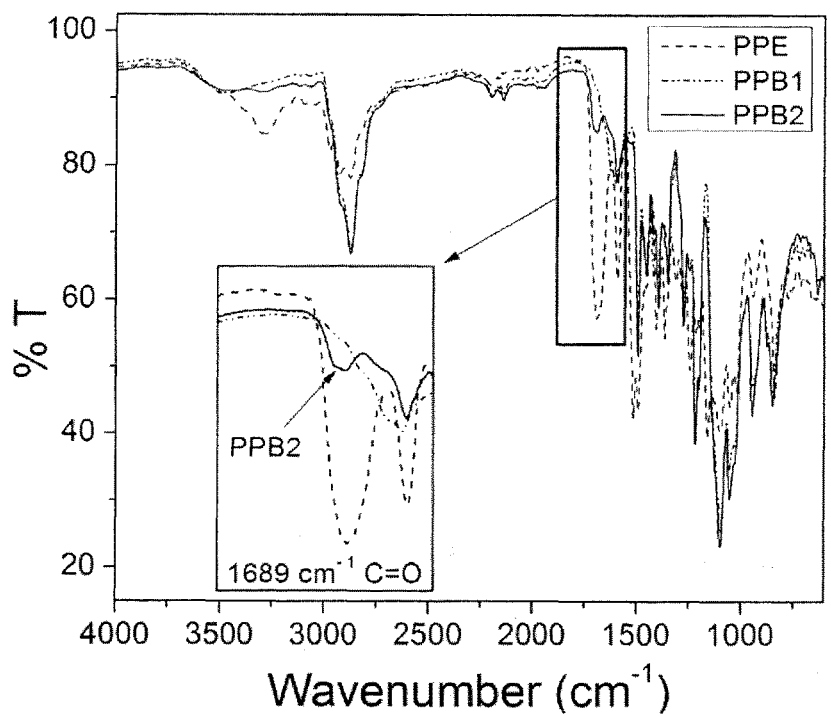
FIGS. 8A-8C show a composite of normalized FTIR spectra (FIG. 8A), a composite of normalized absorption spectra (FIG. 8B), and a composite of normalized emission spectra of polymers PPB, PPE, and PE-dPPB for various co- and terpolymer PPEs (FIG. 8C) according to an embodiment of the invention.
Figure 8B:
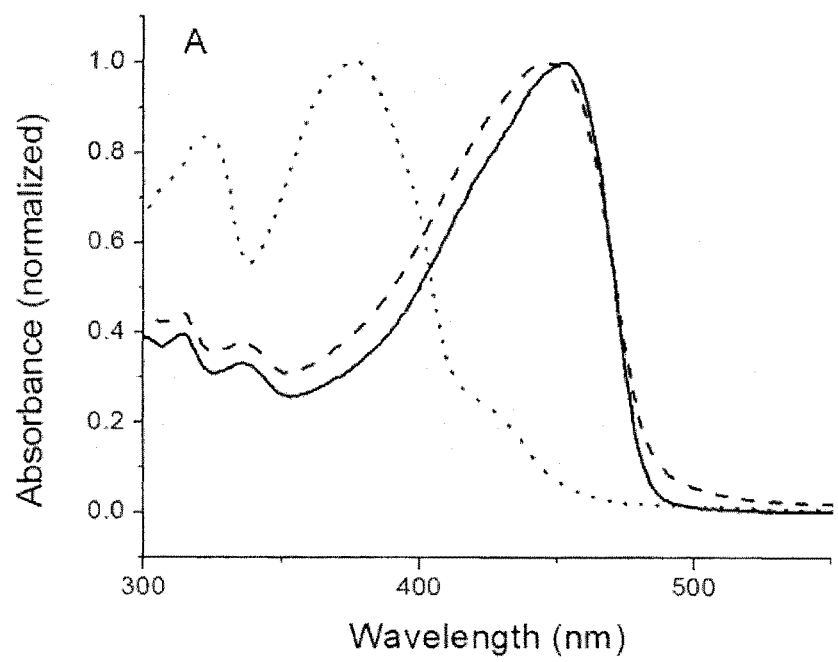
Figure 8C:
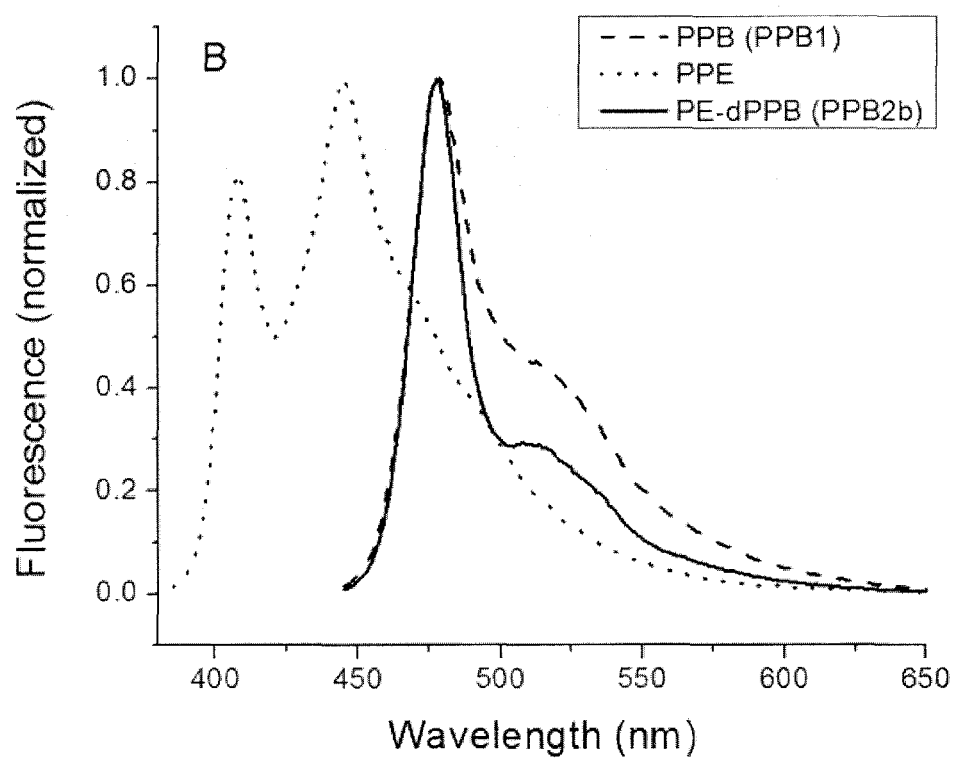

In other embodiments of the subject invention, the flexible linker is provided by a diacetylide monomer or the dihaloaryl monomer. The use of a monomer with a flexible linker between two aryl halides is shown in FIG. 5, where the monomer is prepared as shown in FIG. 6. In this embodiment of the invention, the conjugation length depends upon the coupling conditions, where a Glaser coupling promotes long conjugation sections from the coupling of diacetylene monomers, and short (trimer) conjugation lengths from Sonogashira coupling. A proton NMR spectrum of a polymer made as indicated in FIG. 5 is shown in FIG. 7. Composite FTIR, absorbance, and emission spectra, for the different PPEs formed by Glaser coupling, Sonogashira coupling, and competitive coupling is shown in FIGS. 8A, 8B, and 8C, and summarized in Table 3, below.

Figure 9:
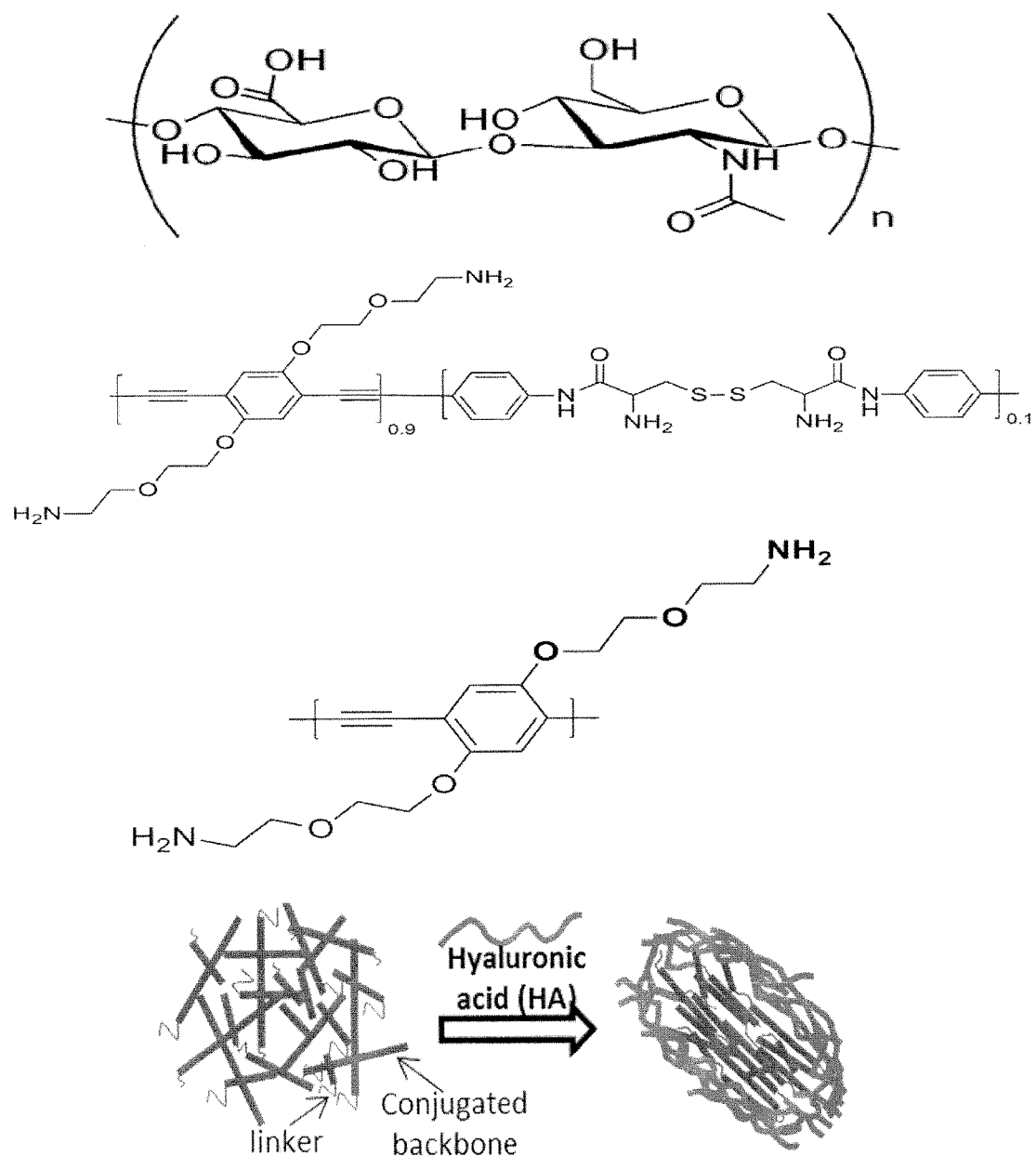
FIG. 9 shows structures for the components and a scheme for the formation of a complex between hyaluronic acid and an amine substituted PPE, according to an embodiment of the invention.
Figure 10A:
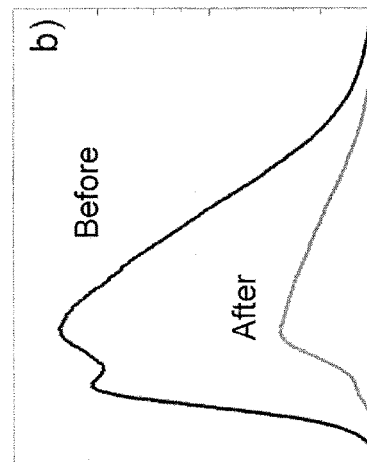
FIGS. 10A-10D show composite absorption and emission spectra, FIG. 10A and FIG. 10B of uncomplexed and hyaluronic acid complexed PE-d-PPB, respectively.
Figure 10B:
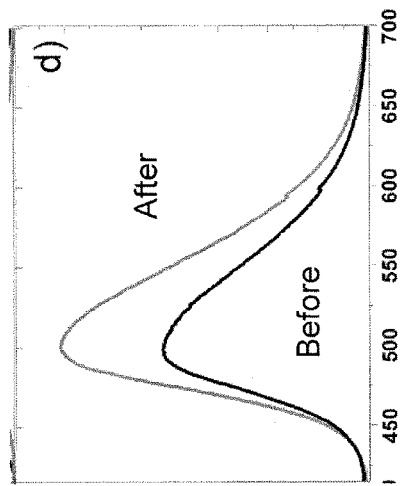
Figure 10C:
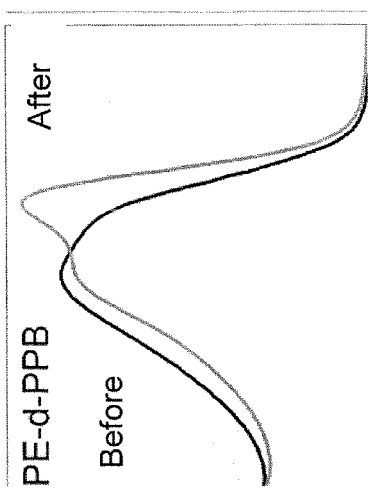
Figure 10D:
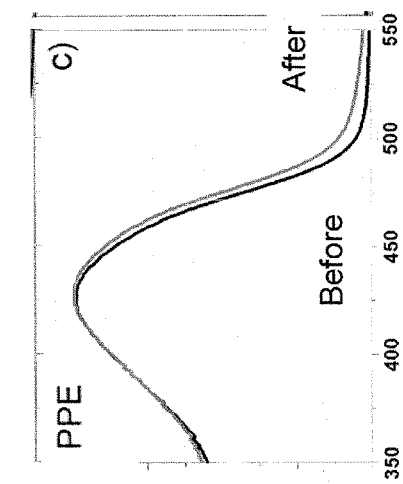
Figure 11B:
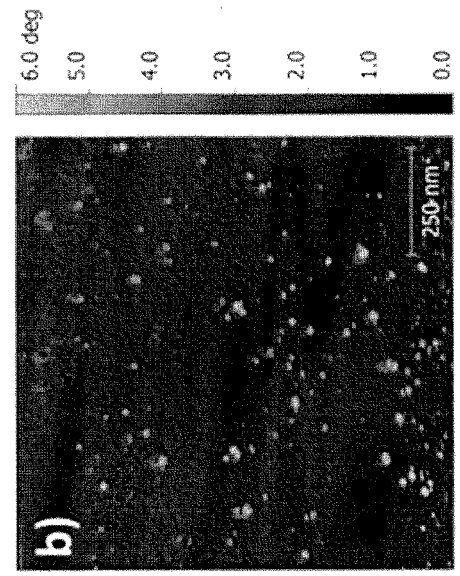
FIGS. 11A-11D shows micrographs of PPE-hyaluronic acid complexed nanoparticles according to an embodiment of the invention.
Figure 11D:
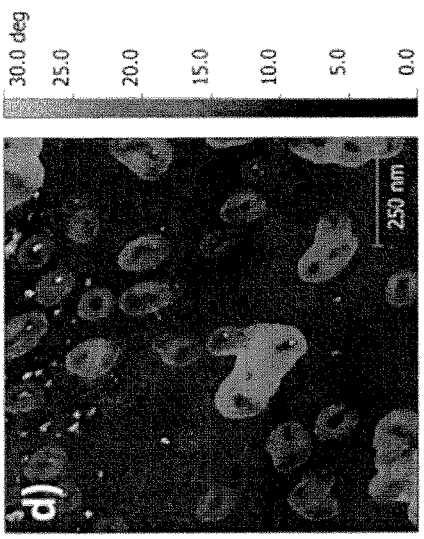
Figure 11A:
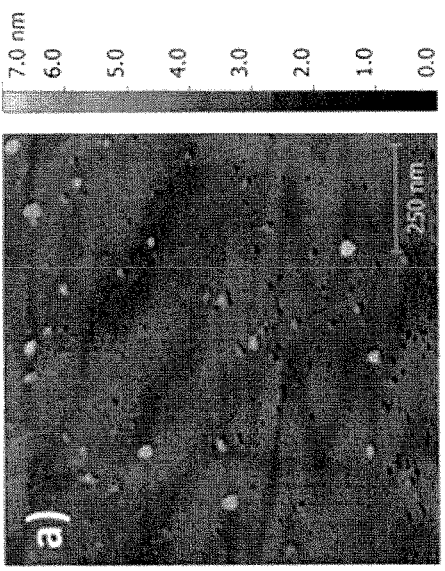
Figure 11C:
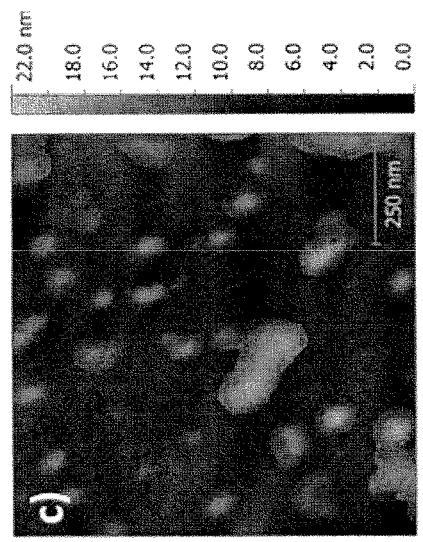

In an embodiment of the invention, PPEs with flexible linkers form complexes between the amines and carboxylic acid groups of polymers, including biopolymers, for example, a complex with hyaluronic acid, as illustrated in FIG. 9. The complexation can be observed by absorption and emission spectroscopy, as is readily observed by the spectra illustrated in FIGS. 10A-10D. The complexation from solution results in the formation of nanoparticles, as shown in FIGS. 11A-11D.

Figure 12A:
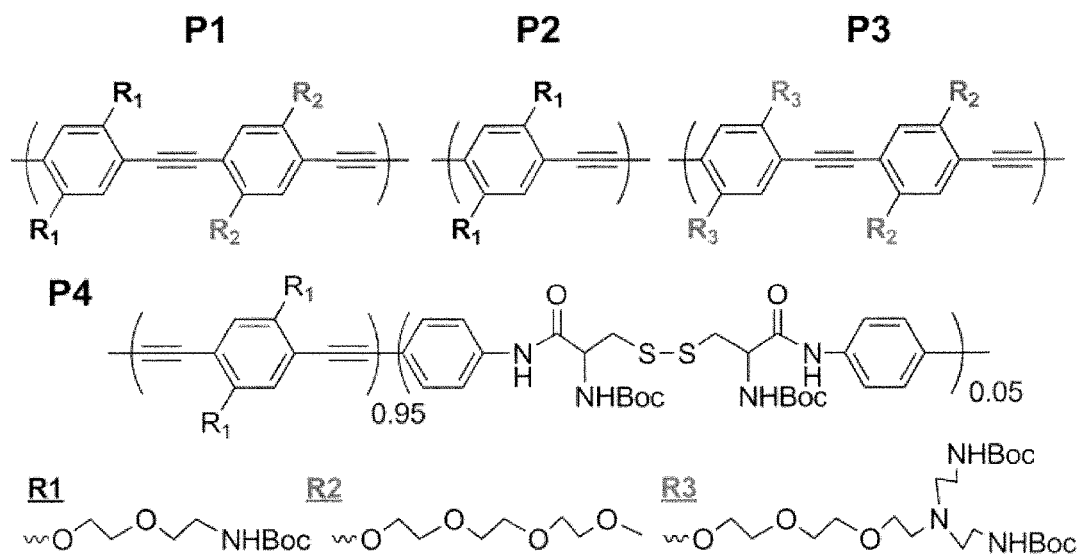
FIG. 12A and FIG. 12B shows the structures of PPEs which leads to the Golgi localization affinities (FIG. 12A) that are plotted in FIG. 12B.
Figure 12B:
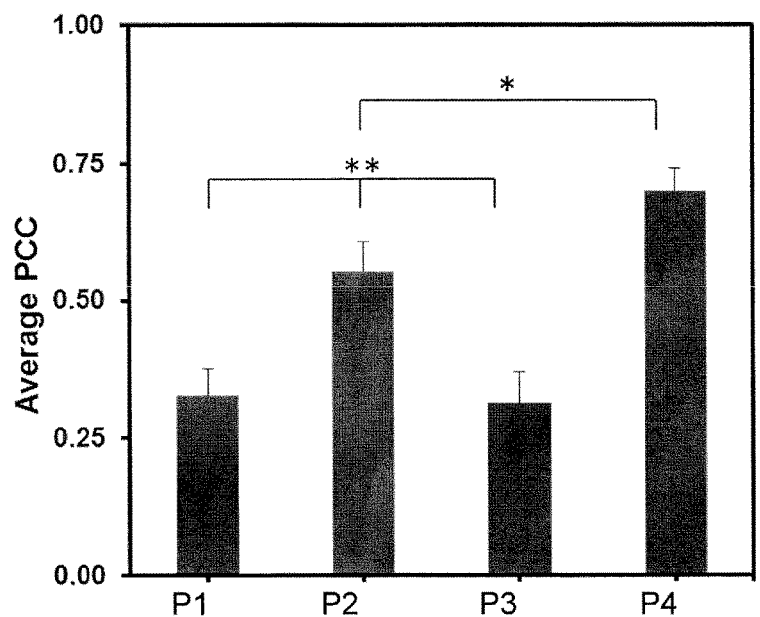
Figure 13:
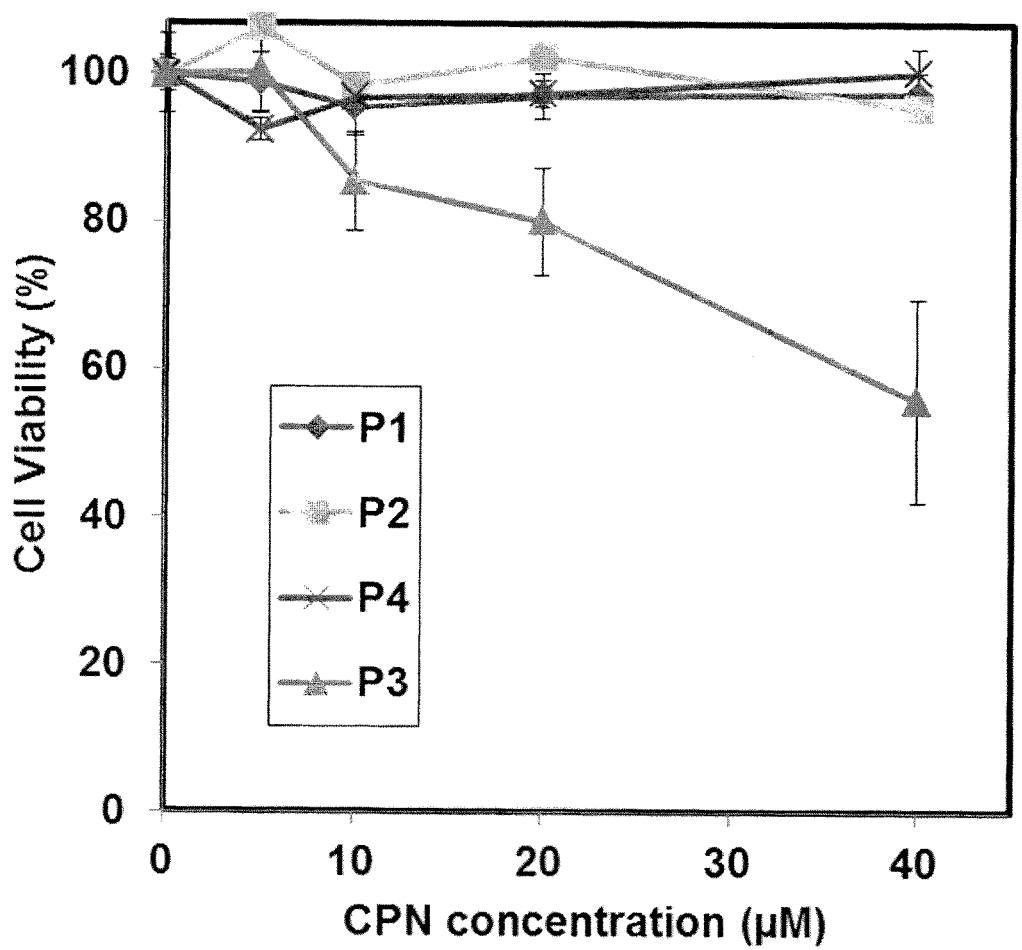
FIG. 13 shows a plot of cell viability for their exposure to the PPEs of FIG. 12A according to an embodiment of the invention.

The PPEs with flexible linkers, according to an embodiment of the invention, is modified by the side groups attached to the aromatic units of the polymers. For example, as can be seen in FIG. 12A, the structure can be varied, and depending on the polymers microstructure, the structural variation leads to selectivity of the polymers for specific cells, as indicated the golgi localization selectivity illustrated in FIG. 12B. The structures and photophysical properties for the polymers of FIG. 12A are tabulated in Table 3, below. The functional groups effect toxicity to cells depending on the side groups, is shown in FIG. 13.

TABLE 3

Structures and properties of polymers prepared from competitive Glaser and Sonogashira coupling.

Figure 15:
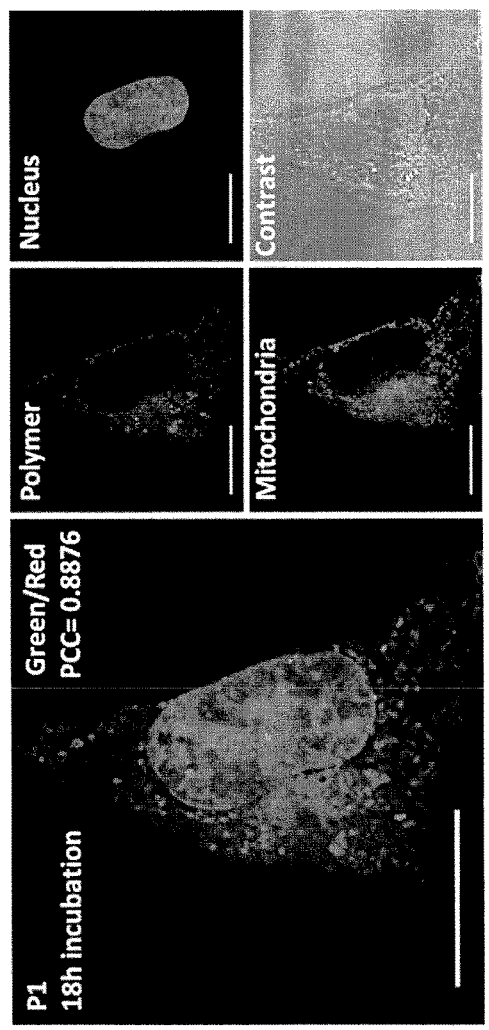
FIG. 15 shows microscopic images of HeLa cells incubated with P10 for 18 hours followed by mitochondrial (red) and nuclear (blue) staining, where the scale bar is 20 μm and PCC values of 0 and 1 correspond to uncorrelated and perfectly linear correlated images, respectively, that demonstrate strong co-localization of P10 and mitochondrial organelles according to an embodiment of the invention.

| CPN | Type | $M_n$ (kDa)[a] | PDI[b] | Abs $\lambda_{max}$[c] (nm) | Emission $\lambda_{max}$[d] (nm) | Quantum Yield[e] | Hydrodynamic radius (d · nm)[f] | Zeta Potential (mV)[f] |
|---|---|---|---|---|---|---|---|---|
| P1 | PPE | 11.8 | 1.43 | 427 | 492 | 2% | 71.22 | +42.3 |
| P2 | PPE | 16.4 | 1.49 | 433 | 496 | 3% | 60.55 | +20.2 |
| P3 | PPE | 10.7 | 1.64 | 420 | 496 | 2% | 58.34 | +44.3 |
| P4 | PE-d-PPB | 22.3 | 2.28 | 444 | 500 | 1% | 87.41 | +46.2 | bation of human cervical carcinoma (HeLa) cells, P10 was primarily observed to be at perinuclear regions and exhibited almost complete overlap with mitotracker stained mitochondria, as shown in FIG. 15. Subcellular localization of P10 was monitored using wide-field fluorescent microscopic imaging and quantitative co-localization information was obtained from the micrographs using the Pearson's Correlation Coefficient (PCC) method, a probe-independent method that gauges co-localization between two dyes by measuring the pixel-by-pixel covariance in the signals.

The observed mitochondrial-specificity appears to be due to the incorporation of the disulfide-containing biodegradable linker to the CPN backbone. Upon internalization, the polymer is actively internalized into the cell via an endocytotic pathway that is common to this class of materials. Upon interaction of the polymer with intracellular glutathione, it is degraded to oligomers that are actively trafficked to the mitochondria. A control CPN P20, which did not contain the biodegradable linker, shown in FIG. 14 where x:y is 1:0. Following synthesis and characterization, the polymers were suspended in water affording CPNs that were physically stable in water. Physicochemical properties of CPNs are listed in Table 4, below. The lower molecular weight P10 afforded the larger particle compared to P20. Although the polymers afforded different size CPNs, the difference in hydrodynamic radius is expected to have minimal effects on the cellular interaction and subcellular localization due to the polydisperse nature of CPNs.

TABLE 4

Photophysical and physical properties of polymers

| Polymer | $Mn^a$ (kDa) | PDI[b] | $\lambda max^c$, abs (nm) | $\lambda max^d$, em (nm) | QY | Hydrodynamic Diameter[e] (nm) |
|---|---|---|---|---|---|---|
| P10 | 15.98 | 1.65 | 436 | 478 | 0.25 | 67.7 |
| P20 | 9.30 | 1.42 | 405 | 472 | 0.40 | 84.4 |

[a]Determined by gel permeation chromatography in THF relative to polystyrene standard.
[b]Polydispersity index (PDI) = $M_w/M_n$.
[c]Measured in water.
[d]Measured in water, excitation wavelength 400 nm.
[e]Measured by DLS at 500 µM in water. Mean ± standard deviation.

To determine the role the biodegradable linker plays on subcellular localization, P10 and P20 co-localization with various organelles was monitored using wide-field fluorescent microscopic imaging. Mean PCC scores from three independent images of an entire cell were selected and analyzed to increase the analysis objectivity. After 18 h, P10

Figure 14:
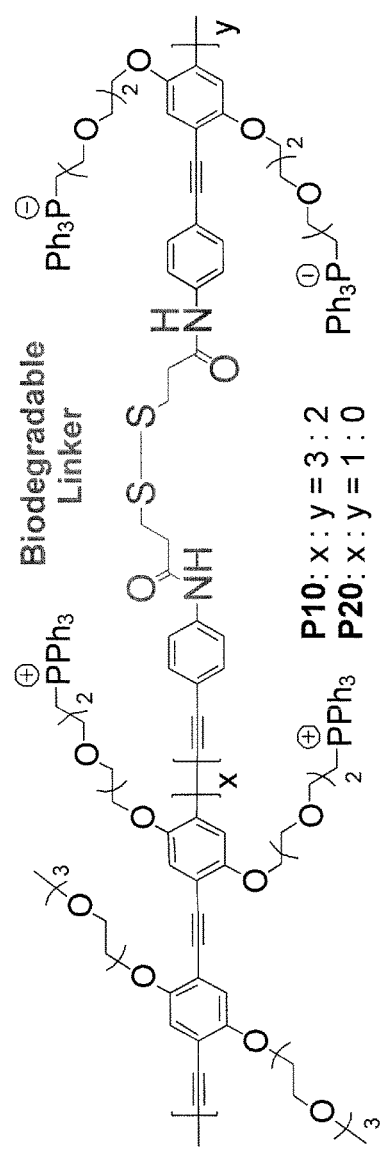
FIG. 14 shows the structures of PPEs with (P10), according to an embodiment of the invention, and without (P20) flexible biodegradable linker units in the backbone.
Figure 16:
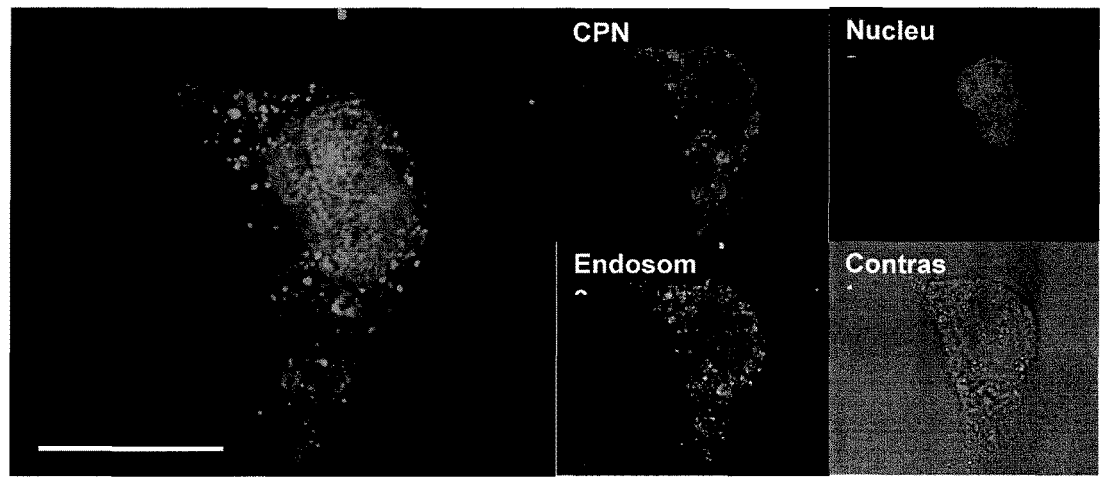
FIG. 16 shows microscopic images of HeLa cells incubated with P20 for 18 hours followed by mitochondrial (red) and nuclear (blue) staining, where the scale bar is 20 μm and PCC values of 0 and 1 correspond to uncorrelated and perfectly linear correlated images, respectively, that demonstrate no co-localization of P20 and mitochondrial organelles.

In an embodiment of the invention, PPEs, such as P10 of FIG. 14, contain a biodegradable linker-containing poly(phenyleneethynylene) with TPP side-chains. These conjugated polymers form nanoparticles (CPNs) that exhibit mitochondria-specific co-localization. After overnight incuexhibited almost exclusive mitochondrial co-localization, as indicated in FIG. 15, with minimal endosomal and Golgi apparatus co-localization. Alternatively, P20 showed minimal mitochondrial and Golgi apparatus co-localization, but strong endosomal co-localization, as indicated in FIG. 16.

Figure 17:
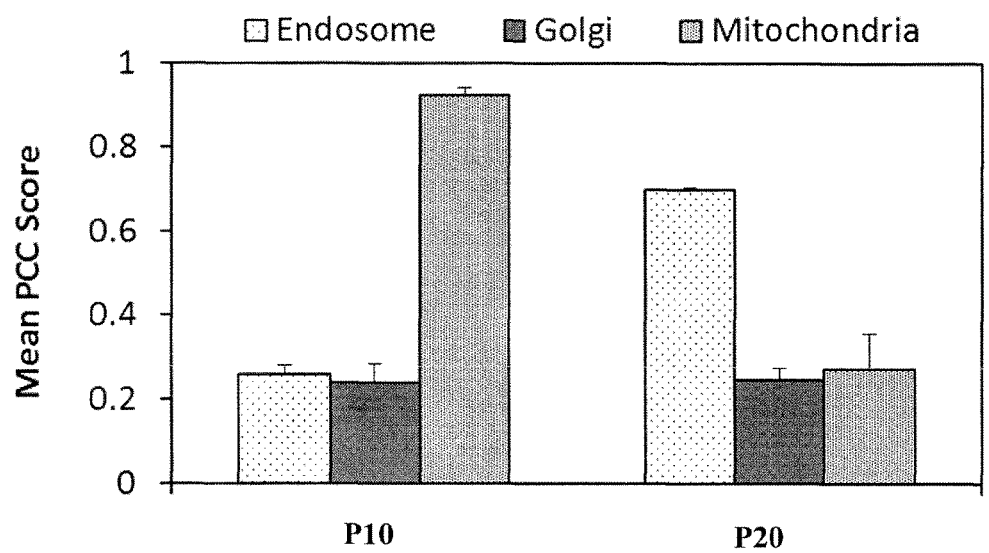
FIG. 17 is a bar graph of the quantitative analysis of co-localization using the PCC algorithm, where error bar represents ±standard deviation (n=3) for an ANOVA-Tukey test that demonstrates statistically different P10 and P20 co-localization with endosome and mitochondria, with $p<0.0005$ when P10 compared with P20.

The Golgi selectivity is indicated in FIG. 17. This significant difference in co-localization provides strong evidence of how the biodegradable linker is playing a role in P10's mitochondrial-specificity. However, depending on the endocytotic entry pathway, the CPN will be trafficked into different organelles, and the significant size difference observed between both CPNs is expected to affect the internalization mechanism.

The endocytosis pathway of both polymers was examined using flow cytometry. The relative amount of CPNs in HeLa cells after two hour incubation was measured in the absence and presence of endocytosis inhibitors. HeLa cells were treated with pharmacological inhibitors for Clathrin-mediated endocytosis (CME), Caveoli-mediated (CvME) endocytosis, or macropinocytosis (MPC) for 30 minutes prior to CPN incubation. P10 and P2 uptake was significantly inhibited by all inhibitors, implying that P10 and P20 are internalized by a variety of endocytosis mechanisms. As expected, P10 exhibited significantly different uptake to P20, exhibiting higher uptake via CvME and MPC. The increased size of P10 may account for the increased MPC uptake, as it has been shown that larger particles are more likely to be engulfed via macropinocytosis than other endocytosis pathway. This increased internalization via MPC membranes can further facilitate endosomal escape and intracellular trafficking of P10 to the mitochondria as macropinosomes have been shown to be highly "leaky". Additionally, increased CvME uptake by caveosomes remains highly beneficial, as trafficking via these non-destructive organelles have been shown to have high intracellular retention.

To determine whether the observed P10 mitochondrial specificity is due to the biodegradable linker or the significant endocytosis pathway, endosome and mitochondrial co-localization for both CPNs was examined as a function of time. Subcellular localization was monitored by fluorescent microscopic imaging, with CPNs incubated for 3, 6, 12, and 18 hours in HeLa cells. PCC co-localization analysis between polymer and mitochondrial or endosomal markers were measured and averaged for three independent images.

Figure 18:
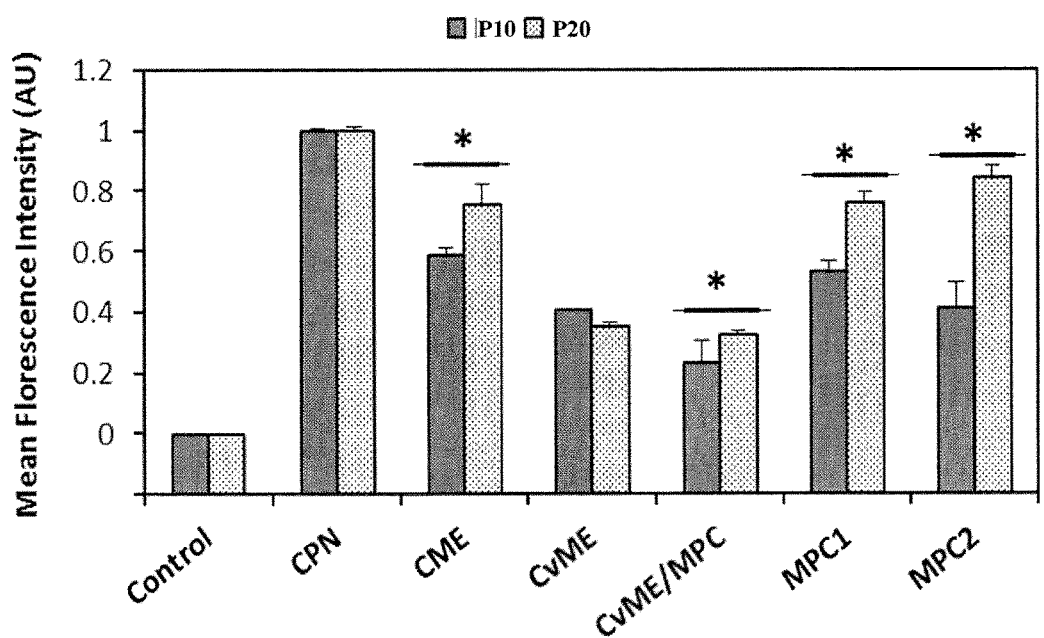
FIG. 18 shows a bar graph of endocytosis inhibition using three independent (n=3) measurements of P10 and P20 at 5 μM concentrations with pharmacological inhibitors was used where the relative amount of CPNs in HeLa cells in the absence (CPN) and presence of pharmacological inhibitors (Control) HeLa cell control where: (CPN) is for CPNs only; (CME) with chlorpromazine (24 mM); (CvME) with genistein (210 µM); (CvME/MPC) with methyl-β-cyclodextrin (1000 mM); (MPC1) with LY294002 (120 µM); and (MPC2) with cytochalasin D (0.04 mM) measured using flow cytometry, as P10 and P20 uptake was significantly inhibited by all inhibitors, and error bars represent standard deviation.*p<0.05 when compared to absence of inhibitor.
Figure 19A:
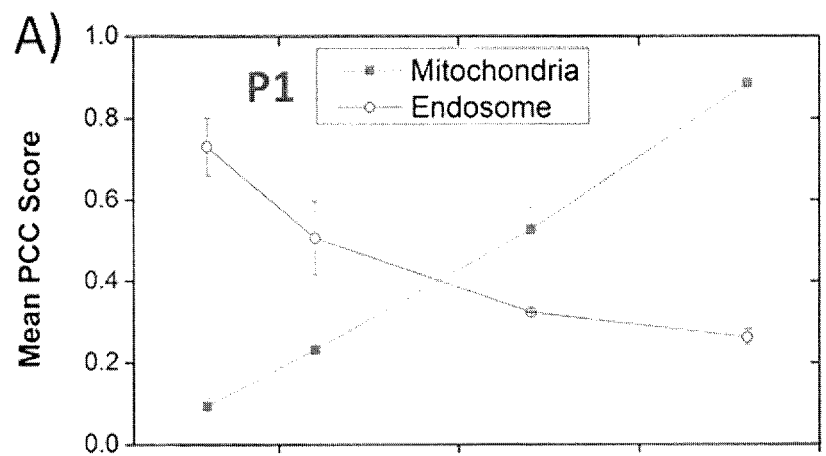
FIG. 19A and FIG. 19B show plots of co-localization of P10 (FIG. 19A), and P20 (FIG. 19B) with endosomes and mitochondria over an 18 hour period using quantitative analysis using the PCC algorithm for three independent (n=3) images, where
Figure 19B:
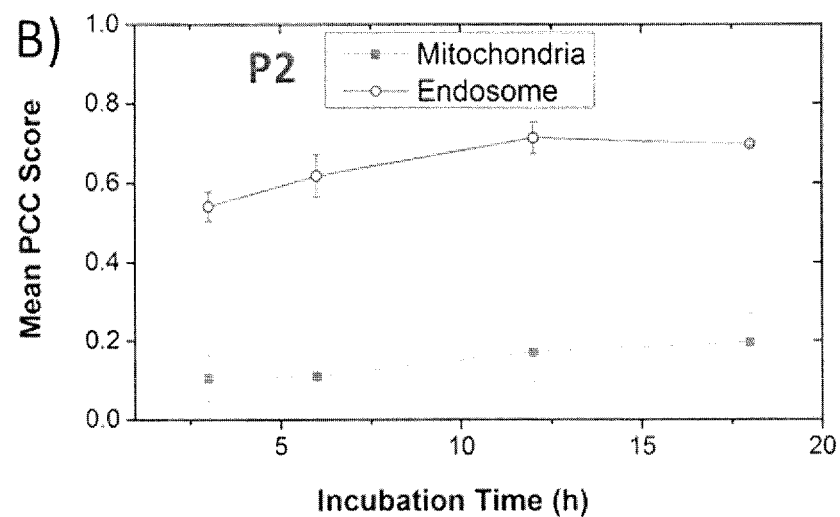

Mean PCC values were plotted as a function of time, as shown in FIG. 18. P10 exhibited a time-dependent mitochondrial and endosomal co-localization; as incubation time increased, P10 co-localized more strongly towards the mitochondria, with almost exclusive mitochondrial co-localization at 18 hours incubation, as indicated in FIG. 19A. As expected, P20 did not show time-dependent co-localization, exhibiting no significant change in mitochondrial or endosomal co-localization as incubation time increased, as indicated in FIG. 19B. P10's time-dependent co-localization strongly supports that degradation of biodegradable linker is taking place, and therefore, playing a significant role in P10's mitochondrial trafficking.

All publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

What is claimed is:

1. A conjugated polymer, comprising a poly(p-phenyleneethynylene) (PPE) having a flexible linker between a portion of phenylene units, having the structure:

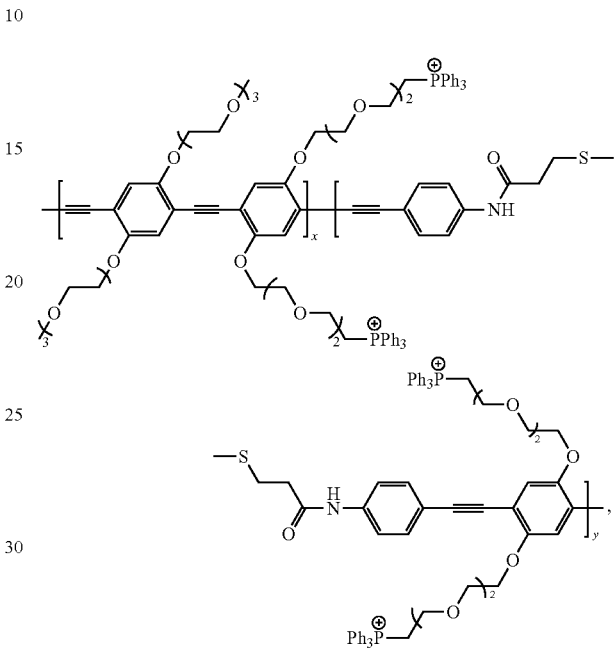

wherein x is 0.1 y to 10 y, and wherein x+y is 2 to 100,000.

2. The conjugated polymer according to claim 1, further comprising at least an additional repeating unit from the structure:

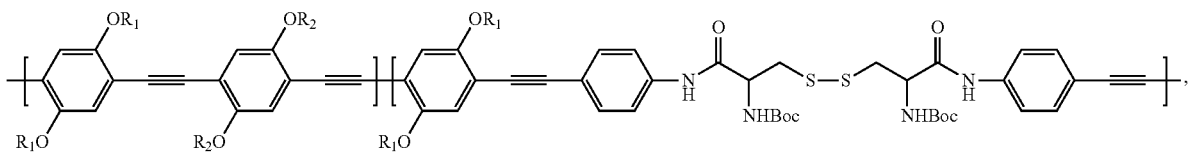

wherein R1 and R2 are independently a polyethyleneoxide oligomer or an alkyl group, optionally terminated with a functionality comprising at least one amine, carboxylic acid, thiol, hydroxy, or any combination thereof.

3. The conjugated polymer according to claim 2, wherein $R_1$ and $R_2$ are:

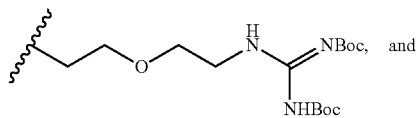

-continued

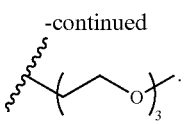

4. The conjugated polymer according to claim 2, further comprising a complex with a molecule through a complementary functionality to at least one of $R_1$ and $R_2$.

5. The conjugated polymer according to claim 4, wherein the molecule is a biopolymer.

6. The conjugated polymer according to claim 4, wherein the molecule is a polysaccharide.

7. The conjugated polymer according to claim 6, wherein the polysaccharide is hyaluronic acid, chondroitin sulfate, dermatin, or heparine sulfate.

8. The conjugated polymer according to claim 4, wherein the complex is in the form of a nanoparticle.

9. The conjugated polymer according to claim 1, wherein the conjugated polymer is in the form of a nanoparticle.

10. An intracellular organelle targeting reagent, comprising the conjugated polymer according to claim 1.

11. A method of preparing a conjugated polymer according to claim 1 comprising:
  providing at least one diacetylene substituted phenylene monomer and/or at least one dihalo substituted phenylene monomer;
  providing at least one monomer comprising a flexible linker at least two phenylenes substituted with acetylene functionality or halo phenylene functionality;
  providing a Sonogashira catalyst; and
  combining the at least one diacetylene substituted phenylene monomer and/or at least one dihalo substituted phenylene monomer with the at least one monomer comprising a flexible linker with the Sonogashira catalyst, wherein condensation occurs to form the conjugated polymer according to claim 1.

12. A method of preparing a conjugated polymer according to claim 2 comprising:
  providing at least one diacetylene substituted phenylene monomer and/or at least one dihalo substituted phenylene monomer;
  providing at least one monomer comprising a flexible linker at least two phenylenes substituted with acetylene functionality or halo phenylene functionality;
  providing a Sonogashira catalyst; and
  combining the at least one diacetylene substituted phenylene monomer and/or at least one dihalo substituted phenylene monomer with the at least one monomer comprising a flexible linker with the Sonogashira catalyst, wherein condensation occurs to form the conjugated polymer according to claim 2.

* * * * *